United States Patent [19]

Koshino et al.

[11] Patent Number: 4,918,052

[45] Date of Patent: Apr. 17, 1990

[54] PERFUME BASE COMPOSITION

[75] Inventors: Junji Koshino; Yoshiaki Fujikura, both of Utsunomiya; Manabu Fujita, Kashiwa; Nao Toi, Sakura, all of Japan

[73] Assignee: Kao Corporation, Tokyo, Japan

[21] Appl. No.: 301,832

[22] Filed: Jan. 26, 1989

[30] Foreign Application Priority Data

Jan. 28, 1988 [JP] Japan ................................. 63-18387

[51] Int. Cl.$^4$ .............................................. A61K 7/46
[52] U.S. Cl. ................................................... 512/22
[58] Field of Search ........................... 568/420; 512/22

[56] References Cited

U.S. PATENT DOCUMENTS

| | | | |
|---|---|---|---|
| 2,710,825 | 6/1955 | Lazier et al. ........................... | 512/22 |
| 2,746,993 | 5/1956 | Dean ..................................... | 568/420 |
| 3,940,446 | 2/1976 | Kahn ..................................... | 568/420 |
| 4,122,121 | 10/1978 | Gray et al. ........................... | 568/420 |

FOREIGN PATENT DOCUMENTS

| | | | |
|---|---|---|---|
| 92031 | 10/1983 | European Pat. Off. ............ | 568/420 |
| 59-204115 | 11/1984 | Japan ..................................... | 512/22 |
| 21367 | of 1912 | United Kingdom ................ | 568/426 |

OTHER PUBLICATIONS

J. Org. Chem., vol. 32, p. 113 (1967).
J. Org. Chem., vol. 43, p. 3792 (1978).
Rozhkovskaya et al, Chem. Abst., vol. 91, #103218k (1979).

*Primary Examiner*—James H. Reamer
*Attorney, Agent, or Firm*—Oblon, Spivak, McClelland, Maier & Neustadt

[57] ABSTRACT

A perfume base composition containing 2-cyclohexylpropanal is disclosed. 2-Cyclohexylpropanal can be prepared by subjecting 2-cyclohexylpropanol to liquid-phase dehydrogenation.

1 Claim, No Drawings

PERFUME BASE COMPOSITION

BACKGROUND OF THE INVENTION (1) Field of the Invention

This invention relates to a perfume base composition, and more specifically to a perfume base composition containing 2-cyclohexylpropanol and having no allergic effects.

(2) Description of the Related Art

Japanese Patent Application Laid-Open No. 204115/1984 discloses that the following compounds:

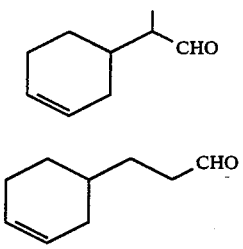

give off fresh green fragrance and are excellent as perfume bases for soaps, detergents and cosmetics. According to the above patent publication, the above compounds are said to be obtained as an about 2:8 mixture by an oxo reaction among 4-vinylcyclohexene-1, carbon monoxide and hydrogen.

Subsequent investigations have however revealed that the above compounds have cutaneous allergic effects. They have hence been found to involve a safety problem for their use as perfume bases for soaps, detergents and cosmetics.

As will be described herein, the perfume base composition according to the present invention comprises 2 cyclohexylpropanol. 2-Cyclohexylpropanol can be prepared, for example, by the following process (A) described in J. Org. Chem., 32, 113 (1967):

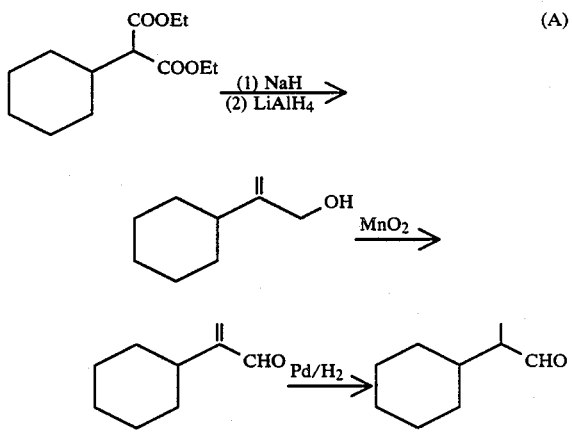

or by the following process (B) disclosed in J. Org. Chem., 43, 3792 (1978):

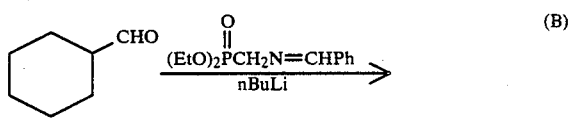

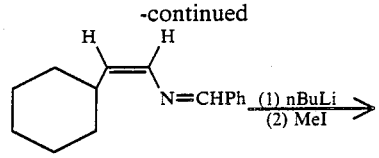

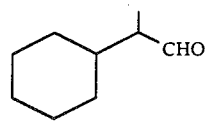

These processes are however not considered to be industrial processes from the viewpoint of the number of reaction steps and the yield of the final compound.

SUMMARY OF THE INVENTION

With the foregoing in view, the present inventors have carried out an extensive investigation with a view toward finding out a perfume base having excellent fragrance without any problem with respect to its safety. As a result, it has been unexpectedly found that 2-cyclohexylpropanol represented by the following formula:

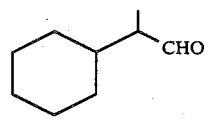

gives off fragrance resembling fresh citrus green, matches well with other fragrance components and imparts sweet, rich and pleasant fragrance when incorporated in conventional formulated perfume bases, and moreover is free of allergic effects, leading to completion of this invention.

In one aspect of this invention, there is thus provided a perfume base composition which comprises 2-cyclohexylpropanol.

The present inventors hence contemplated of obtaining the target compound by oxidizing 2-hexylpropanol which is industrially available with industrial standpoint, an investigation has been conducted on liquid-phase dehydrogenation having such merits that no special equipment is required and waste materials are not very troublesome. As a result, it has been found surprisingly that although conversions as low as about 30-35% are only available in conventional liquid-phase dehydrogenation reactions, a conversion as high as 67% is achieved in the case of the compound according to this invention and its selectivity is as high as 91%.

In another aspect of this invention, there is also provided a novel preparation process for the compound useful in the novel perfume base composition, namely, a process for the preparation of 2-cyclohexylpropanol, which comprises subjecting 2-cyclohexylpropanol to liquid-phase dehydrogenation.

The present invention has made it possible to prepare 2-cyclohexylpropanol advantageously on an industrial scale. In addition, the perfume base composition according to this invention can impart sweet, rich and pleasant fragrance to formulated perfume bases owing to the fresh-citrus-green-like fragrance of 2-cyclohexylpropanol and are also useful as a perfume base for soaps, detergents, cosmetics and the like.

The above and other objects, features and advantages of the present invention will become apparent from the following description and the appended claims.

DETAILED DESCRIPTION OF THE INVENTION AND PREFERRED EMBODIMENTS

The process of this invention can be practised by heating 2-cyclohexylpropanol in the presence of a dehydrogenation catalyst in a solvent.

Illustrative examples of the dehydrogenation catalyst may include copper, silver, zinc, copper-zinc, copper-chromium, and the like. Preferably, the catalyst may be used in a proportion of 0.001–10 wt. % based on 2-cyclohexylpropanol.

Liquid paraffin is preferred as the solvent. It is preferable to use liquid paraffin in an amount of 10–500 times the weight of the catalyst.

The reaction may be conducted by suspending the dehydrogenation catalyst in the solvent and then feeding 2-cyclohexylpropanol continuously while distilling out the reaction product or adding 2-cyclohexylpropanol batchwise. The reaction pressure may be either normal pressure or reduced pressure.

Upon purification of the reaction mixture by distillation subsequent to the reaction, 2-cyclohexylpropanol can be easily obtained with high purity. 2-Cyclohexylpropanol which is also recovered by the distillation can be used again as the starting material.

2-Cylohexylpropanol according to this invention can be used as a safe perfume base free of cutaneous allergic effects in soaps, detergents, cosmetics, etc.

The perfume base composition according to this invention may be formulated preferably by incorporating 2-cyclohexylpropanol to a content of about 0.01–10 wt. % of the whole composition.

This invention will next be described by the following Examples.

EXAMPLE 1

Under a nitrogen stream, 0.3 g of Cu-Cr catalyst and 300 ml of liquid paraffin were charged in a 1-l four-necked flask equipped with a mechanical stirrer, a dropping funnel, a nitrogen inlet tube and a Claisen head distillation equipment. The internal temperature of the flask was raised to 250° C. To the flask, 2-cyclohexylpropanol was added through the dropping funnel at a rate of 5 g per hour to a total amount of 100 g. During that time, 70 g of a mixture of the reaction product and starting material was distilled out. After lowering the internal temperature to 120° C., the internal pressure was reduced to 5 mmHg so that a distillate was obtained in an amount of 24 g. After combining those two distillates, the resultant mixture was analyzed by gas chromatography. The mixture was found to contain 64% of 2-cyclohexylpropanol and 35% of unreacted 2-cyclohexylpropanol. The mixture was distilled by a 5-tray distillation column to obtain 60 g of 2-cyclohexylpropanol (purity: 98.7%; boiling point: 65° C./5 mmHg) and 33 g of 2-cyclohexylpropanol (purity: 97.8%; boiling point: 92° C./5 mmHg). Conversion and selectivity were 67% and 91% respectively. 2-Cyclohexylpropanol:

IR (liquid film): 2930, 2855, 2700, 1725 and 1458 $cm^{-1}$.

NMR ($CDCl_3$, δ, TMS as internal standard): 1.00 (3H, d, J=6 Hz), 0.7–1.9 (11H, m), 2.20 (1H, m), and 9.65 (1H, d, J=2 Hz) ppm.

EXAMPLE 2

With respect to 2-cyclohexylpropanol and the 2:8 mixture disclosed in Japanese Patent Application Laid-Open No. 204115/1984, a test on their cutaneous allergic effects was conducted based on the CCET (Cumulative Contact Enhancement Test) method. Results are summarized in Table 1. It has been confirmed that 2-cyclohexylpropanol does not have cutaneous allergic effects and is hence safe.

TABLE 1

| Induction: 5% in EtOH | | Challenge Concentrations | |
|---|---|---|---|
| | | 3% | 10% |
| 2-Cyclohexylpropanol | Number of sensitized animals Average skin reaction | 0/10 0 | 0/10 0.3 |
| Mixture described in Patent Application Laid-Open No. 204115/1984 | Number of sensitized animals Average skin reaction | 1/10 0.6 | 6/10 1.5 |

EXAMPLE 3

| Formulated Perfume Base for dish wash | |
|---|---|
| Lemon Oil California | 100 (parts by weight) |
| Orange Oil Valencia | 200 |
| Limonene | 653 |
| Aldehyde C-8 | 5 |
| Aldehyde C-10 | 2 |
| Citral | 10 |
| Nellol | 10 |
| Methyl dihydrojasmonate | 10 |
| | 990 |

Addition of 10 parts by weight of 2-cyclohexylpropanol to 990 parts by weight of the above formulated perfume base provided a formulated perfume base for dish wash enhanced further in fresh and natural feeling.

We claim:

1. A perfume base composition comprising 2-cyclohexylpropanol in a mixture with conventional perfume base components.

* * * * *

UNITED STATES PATENT AND TRADEMARK OFFICE
CERTIFICATE OF CORRECTION

PATENT NO. : 4,918,052
DATED : April 17, 1990
INVENTOR(S) : KOSHINO et al.

It is certified that error appears in the above-identified patent and that said Letters Patent is hereby corrected as shown below:

At column 1, lines 38-39 and 39;

At column 2, lines 24, 42, 58, 62 and 67;

At column 3, lines 26, 30, 35 and 56; and

At column 4, lines 2, 6, 14, 21, 27, 49 and 55:

"2-cyclohexylpropanol" should read:

--2-cyclohexylpropanal--.

Signed and Sealed this

Twelfth Day of May, 1992

Attest:

DOUGLAS B. COMER

*Attesting Officer*   *Acting Commissioner of Patents and Trademarks*